United States Patent
Trumbore et al.

(10) Patent No.: US 9,278,066 B2
(45) Date of Patent: Mar. 8, 2016

(54) TOPICAL PHARMACEUTICAL FOAM COMPOSITION

(71) Applicant: Precision Dermatology, Inc., Cumberland, RI (US)

(72) Inventors: Mark W. Trumbore, Westford, MA (US); Ronald M. Gurge, Franklin, MA (US); Jane C. Hirsh, Wellesley, MA (US)

(73) Assignee: Precision Dermatology, Inc., Bridgewater, NJ (US)

( * ) Notice: Subject to any disclaimer, the term of this patent is extended or adjusted under 35 U.S.C. 154(b) by 103 days.

(21) Appl. No.: 14/159,767

(22) Filed: Jan. 21, 2014

(65) Prior Publication Data

US 2014/0134112 A1 May 15, 2014

Related U.S. Application Data

(63) Continuation of application No. 11/552,457, filed on Oct. 24, 2006, now abandoned.

(60) Provisional application No. 60/729,788, filed on Oct. 24, 2005.

(51) Int. Cl.

| | |
|---|---|
| A61K 31/70 | (2006.01) |
| A61K 31/7056 | (2006.01) |
| A61K 31/40 | (2006.01) |
| A61K 9/12 | (2006.01) |
| A61K 9/00 | (2006.01) |
| A61K 9/06 | (2006.01) |
| A61K 31/17 | (2006.01) |
| A61K 31/19 | (2006.01) |
| A61K 31/203 | (2006.01) |
| A61K 38/48 | (2006.01) |
| A61K 45/06 | (2006.01) |
| A61K 47/18 | (2006.01) |

(52) U.S. Cl.
CPC .............. *A61K 9/122* (2013.01); *A61K 9/0014* (2013.01); *A61K 9/06* (2013.01); *A61K 9/12* (2013.01); *A61K 9/124* (2013.01); *A61K 31/17* (2013.01); *A61K 31/19* (2013.01); *A61K 31/203* (2013.01); *A61K 38/4873* (2013.01); *A61K 45/06* (2013.01); *C12Y 304/22002* (2013.01); *A61K 47/18* (2013.01)

(58) Field of Classification Search
CPC ... A61K 45/06; A61K 47/18; A61K 2300/00; A61K 31/203; C12Y 304/22002
See application file for complete search history.

(56) References Cited

U.S. PATENT DOCUMENTS

| | | | |
|---|---|---|---|
| 4,808,388 A | 2/1989 | Beutler et al. | |
| 5,224,183 A | 6/1993 | Dugan | |
| 5,431,913 A | 7/1995 | Phillips | |
| 5,601,838 A | 2/1997 | Hind | |
| 6,126,920 A | 10/2000 | Jones et al. | |
| 6,429,231 B1 | 8/2002 | Bhagwat et al. | |
| 6,586,483 B2 | 7/2003 | Kolb et al. | |
| 6,905,675 B2 | 6/2005 | Shacknai et al. | |
| 6,977,081 B1 | 12/2005 | Rood | |
| 8,592,380 B2 | 11/2013 | Trumbore et al. | |
| 2004/0151671 A1 | 8/2004 | Abram et al. | |
| 2004/0204492 A1 | 10/2004 | Shroot et al. | |
| 2004/0241099 A1 | 12/2004 | Popp et al. | |
| 2005/0031547 A1 | 2/2005 | Tamarkin et al. | |
| 2005/0036950 A1 | 2/2005 | Jones et al. | |
| 2005/0042182 A1 | 2/2005 | Arkin et al. | |
| 2005/0255048 A1 | 11/2005 | Hirsh et al. | |
| 2006/0140984 A1 | 6/2006 | Tamarkin et al. | |
| 2006/0188449 A1 | 8/2006 | Hirsh et al. | |
| 2006/0233721 A1 | 10/2006 | Tamarkin et al. | |
| 2006/0275218 A1 | 12/2006 | Tamarkin et al. | |
| 2007/0036731 A1 | 2/2007 | Hirsh et al. | |
| 2007/0154402 A1 | 7/2007 | Trumbore et al. | |
| 2010/0202978 A1 | 8/2010 | Gurge et al. | |
| 2011/0236321 A1 | 9/2011 | Trumbore et al. | |
| 2012/0128598 A1 | 5/2012 | Trumbore et al. | |

FOREIGN PATENT DOCUMENTS

| | | |
|---|---|---|
| EP | 1 468 678 | 10/2004 |
| WO | WO-85/01876 | 5/1985 |
| WO | WO-96/03115 | 2/1996 |
| WO | WO-2004/037225 | 5/2004 |
| WO | WO-2004/064833 | 8/2004 |

(Continued)

OTHER PUBLICATIONS

"Clenia Foaming Wash" http://www.upsher-smith.com Feb. 7, 2005, Retrieved from the Internet: URL:http://www.upsher-smith.com/products/dermatology.html.

(Continued)

*Primary Examiner* — Mina Haghighatian

(74) *Attorney, Agent, or Firm* — John E. Thomas, Esq.; Harter Secrest & Emery LLP

(57) ABSTRACT

A stable topical alcohol-free aerosol foam containing one or more keratolytic agents is provided. The foam-forming formulation is an oil-in-water emulsion which contains one or more hydrofluoroalkane (HFA) propellants and one or more keratolytic agents. The keratolytic agent may be present in either phase of the emulsion or dispersed in the emulsion. The oil phase may consist at least in part of the HFA propellant. The foam is stable on the skin for at least 5 minutes at body temperature and disappears into the skin upon rubbing or after prolonged standing. The formulations may not contain additional co-solvents or non-HFA co-propellants. The formulations demonstrate reduced intensity of the odor and/or color associated with the keratolytic agent(s) as compared to conventional formulations containing keratolytic agents.

8 Claims, No Drawings

(56) References Cited

FOREIGN PATENT DOCUMENTS

| WO | WO-2005/016329 A1 | 2/2005 |
|---|---|---|
| WO | WO-2005/018530 | 3/2005 |
| WO | WO-2005/032522 | 4/2005 |

OTHER PUBLICATIONS

Americaine. Insight Pharmaceuticals Corporation, pp. 1-3. Feb. 5, 2003.
Cetacaine Material Safety Data Sheet (MSDS), Cetylite Industries, pp. 1-4, Aug. 1992.
Cetacaine Topical Anesthetic. Cetylite Industries, pp. 1-3, Nov. 1999.
Dalziel and Creazzo, "Pharmaceutical Aerosols," Spray Technology and Marketing, 6:19-24 (2003).
Gupta et al., "The use of sulfur in dermatology," Journal of Drugs in Dermatology, 3(4):427-431 (2004) Abstract only.
Kibbe et al., "Handbook of pharmaceutical excipients," American Pharmaceutical Association, XP002571593, pp. 560-561 (Jan. 1, 2000).
Physician's Desk Reference, Edition 1995, pp. 933-934 (Sulfacet-R).
Purdon et al., "Foam Drug Delivery in Dermatology: Beyond the Scalp Foam Drug Delivery in Dermatology: Beyond the Scalp," American Journal of Drug Delivery, 1(1):71-75 (2003).
Tarimci et al., "Topical sodium sulfacetamide/sulfur lotion," Journal of Clinical Pharmacy and Therapeutics, 22:301 (1997).
Extended European Search Report dated Apr. 23, 2010 from EP 09162106.
Extended European Search Report dated May 11, 2010 from EP 09162108.6.

ically  designed # TOPICAL PHARMACEUTICAL FOAM COMPOSITION

CROSS-REFERENCE TO RELATED APPLICATIONS

This application is a continuation of U.S. patent application Ser. No. 11/552,457, filed Oct. 24, 2006, which claims the benefit of the priority of U.S. Ser. No. 60/729,788, filed Oct. 24, 2005.

FIELD OF THE INVENTION

This invention is generally in the field of pharmaceutical compositions, specifically pharmaceutical foam compositions containing keratolytic agents intended for topical administration.

BACKGROUND OF THE INVENTION

Pharmaceutical foams are pressurized dosage forms containing one or more active ingredients that, upon valve actuation, emit a fine dispersion of liquid and/or solid materials in a gaseous medium. Foam formulations are generally easier to apply, are less dense, and spread more easily than other topical dosage forms. Foams may be formulated in various ways to provide emollient or drying functions to the skin, depending on the formulation constituents. Accordingly, this delivery technology is a useful addition to the spectrum of formulations available for topical use. However, as yet, only a few pharmaceutical foams are commercially available. Most commercially available foam dosage forms contain corticosteroids, although some products have also been used to deliver antiseptics, antifungal agents, anti-inflammatory agents, local anesthetic agents, skin emollients, and protectants (American Journal of Drug Delivery, 2003, vol. 1(1), pp. 71-75).

There is growing interest in converting non-foam topical treatments to aerosol foam or mousse formulations, which better penetrate the skin, provide faster treatment and do not leave any greasy residue on skin or clothing compared with conventional ointments. Until now, the most common gas propellant used in aerosol products is chlorofluorocarbon (CFC), an ozone-depleting agent. The Montreal Protocol International Treaty, signed by 180 nations, banned the use of chlorofluorocarbons (CFCs) as aerosol propellants and mandated the phasing out of CFC agents. No new or revised aerosol formulations may contain CFC propellants and alternative propellants must be used that are more environmentally friendly. Therefore, manufacturers must reformulate or modify existing products to use non-CFC propellants, while maintaining important aspects of the previous formulation, such as accuracy of delivery, stability, etc. The primary CFC substitute are hydrofluoroalkanes (HFA), also known as hydrofluorocarbons (HFC).

Although hydrocarbon propellants, such as propane and butane, can be used in the manufacturing of pharmaceutical foams, these propellants are not suited for human use since they are flammable. Just as is the case with CFC propellants, hydrofluoroalkanes (HFAs) that possess high chemical stability can be used as a primary substitute for hydrocarbons. Examples of HFAs are 1,1,1,2,3,3,3-heptafluoropropane (HFA-134a) and 1,1,1,2-tetrafluoroethane (HFA-227). Hydrofluoroalkanes (HFAs) are also referred to as hydrofluorocarbons (HFCs) and these terms are used interchangeably.

Since replacing a component of any formulation means introducing new properties, and HFAs differ in their solvating power from CFCs and hydrocarbons, providing reproducible performance of reformulated aerosols for pharmaceutical uses represents a challenging task. Co-solvents (such as ethanol) are often incorporated into the formulation in order to arrive at a stable product (Pharmaceutical Aerosols, June 2003, p. 21). Such formulations, however, have a number of undesirable aspects. Alcohol co-solvents can dry and irritate the skin. U.S. Pat. No. 6,126,920 suggests that the use of alcohol co-solvents can lead to burning, itching, and irritation observed in the use of topical foam for delivering betamethasone. Further, volatile alcohols are highly irritating to mucous membranes.

Formulations that contain volatile alcohols and/or alkanes are potential safety hazards due to the high flammability of the product. Moreover, the flammability characteristics of the product require expensive precautions during manufacturing, and may require controlled environments for storage and for disposal of containers after use. For example, WO 85/01876 describes the fire hazards associated with alcohol- and alkane-containing aerosol foam formulations.

Pharmaceutical foam formulations containing keratolytic agents have not been described in the literature. Keratolytic agents are agents that soften, separate, and cause desquamation (i.e. shedding or peeling) of the cornified epithelium, or horny layer, of the skin. These agents are used to expose mycelia of infecting fungi or to treat corns, warts, and certain other skin diseases. Commonly used keratolytic agents include urea, urea in combination with ammonium lactate, salicylic acid, papain, papain in combination with urea, and sulfur. Sulfur is also used in combination with sodium sulfacetamide to treat acne, rosacea, seborrheic dermatitis, eczema, xerosis, scabies, pediculosis and psoriasis.

Keratolyic agents can be administered in the form of a liquid, cream, lotion or cleanser. Topical formulations containing keratolytic agents typically have an intense color and/or strong odor. For example, sulfur containing products typically have an intense yellow color and/or a strong odor characteristic of sulfur. Urea-containing products frequently exhibit a strong ammonia odor, while papain-containing products exhibit a distinctive papain odor. Current products on the market typically contain substantial amounts of odor masking agents, such as fragrances, in order to mask or shield the odor associated with the pharmaceutical agent. However, the use of high concentrations of fragrances can be problematic. The use of fragrances in topical formulations can result in skin sensitizing reactions in which the patient develops sensitivity to the odor masking agent. Furthermore, the presence of fragrances, which are often complex mixtures of different compounds, may result in undesirable side reactions between the fragrance and the active agent(s).

There exists a need for topical keratolytic foam formulations which, once applied to the skin, have little or no odor or color and are non-staining and which contain little or no odor masking agents such as fragrances.

It is therefore an object of the invention to provide alcohol-free keratolytic topical foam aerosol formulations that use hydrofluoroalkanes (HFAs) as the propellant.

It is a further object of the invention to provide keratolytic topical foam formulations which exhibit reduced intensity of the odor and/or color associated with the keratolytic agent.

BRIEF SUMMARY OF THE INVENTION

A stable topical alcohol-free aerosol foam containing one or more keratolytic agents is described herein. The foam-forming formulation is an emulsion which contains an HFA propellant and one or more keratolytic agents. The formulation optionally contains one or more additional pharmaceutically active agents including, but not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, antiprotozoal agents, anti-oxidants, chemotherapeutic agents, antidepressants, antihistamines, vitamins, sunscreens, skin-soothing agents, hormones, and anti-dandruff agents.

The emulsion contains an oil phase and an aqueous, i.e. water-containing, phase. The active agent(s) may be dissolved in either phase or dispersed in the emulsion. The oil phase may contain, at least in part, the HFA propellant. The foam is stable on the skin, preferably for at least five minutes, more preferably at least twenty minutes, at body temperature, and disappears into the skin upon rubbing or after prolonged standing. The formulations demonstrate reduced intensity of the odor and/or color associated with the keratolytic agent(s) as compared to conventional formulations containing keratolytic agents.

The composition can further contain one or more pharmaceutically acceptable excipients such as surfactants, emollients, emulsifiers, pH stabilizing agents, chelating agents, humectants, stabilizers, preservatives, and combinations thereof, which may be present in the oil phase and/or the aqueous phase. The formulations contain little or no fragrances and/or odor masking agents, thus minimizing the skin sensitizing reactions that can occur due to the presence of such agents.

The inert non-flammable HFA propellant does not require the use of additional co-solvents or co-propellants. Besides their high volatility and vapor pressure, the HFA propellants have been found to provide an additional benefit in terms of reduction of apparent odor of active ingredients, such as sulfur and urea. They also mask color by the formation of stable foams; and leave depots of materials on the skin, which in practice, are less staining to linen and clothing than prior art preparations with the same active ingredients.

In one embodiment the active agent is a keratolytic agent or agents such as urea or urea in combination with ammonium lactate, salicylic acid, papain, and/or sulfur. The keratolytic agent is present in an amount from about 1% to about 60% by weight of the final composition. In another embodiment, the formulation contains a keratolytic agent in combination with an antibiotic. The concentration of the antibiotic is from about 0.01% to about 20%, preferably from about 1% to about 15%, more preferably from about 6% to about 12% by weight of the final composition. In a preferred embodiment, the formulation contains a combination of sulfur and sulfacetamide. In certain embodiments, the amounts of sulfur and sodium sulfacetamide are each from about 0.01% to about 20% (w/w). In certain embodiments, the amounts of sulfur and sodium sulfacetamide are each from about 1% to about 15% (w/w). In certain embodiments, the amounts of sulfur and sodium sulfacetamide are each from about 6% to about 12% (w/w).

In yet another embodiment, the composition includes a proteolytic enzymes such as papain in combination with urea. The concentration of papain is from about 0.5% to about 40%, preferably from about 1% to about 20%, more preferably from about 1% to about 10% by weight of the final composition. The concentration of urea is from about 1% to about 60%, preferably from about 2.5% to about 40%, more preferably from about 5% to about 15% by weight of the final composition. In still another embodiment, the composition includes the enzyme papain in combination with urea and chlorophyllin copper complex sodium. The concentration of papain is from about 0.5% to about 40%, preferably from about 1% to about 20%, more preferably from about 1% to about 10% by weight of the final composition. The concentration of urea is from about 1% to about 60%, preferably from about 2.5% to about 40%, more preferably from about 5% to about 15% by weight of the final composition. The concentration of chlorophyllin copper complex sodium is from about 0.05% to about 5%, preferably from about 0.1% to about 3%, more preferably from about 0.3% to about 1% by weight of the final composition.

The composition can be administered as a continuous or metered dose that can be applied to the skin or mucous membranes.

DETAILED DESCRIPTION OF THE INVENTION

I. Concentrate

A. Propellants

In one embodiment, the propellant is a HFA or a mixture of one or more hydrofluorocarbons. Suitable hydrofluorocarbons include 1,1,1,2-tetrafluoroethane (HFA 134a); 1,1,1,2,3,3,3-heptafluoropropane (HFA 227); and mixtures and admixtures of these and other HFAs that are currently approved or may become approved for medical use are suitable. The concentration of the HFA propellant is from about 5% to about 30% by weight of the concentrate, which corresponds to about 4% to about 23% by weight of the final composition.

Hydrocarbon propellants such as butane/isobutane/propane have inherent, unpleasant odors which may impart negative olfactory sensory attributes to pharmaceutical foam products. When these foam products are dispensed, the propellant expands and evaporates, creating a bubble structure within the foam. It is the evaporative release of the propellant which is detected by the olfactory senses of the user. Therefore, it is advantageous to have a propellant which is odor free and essentially provides no additional base odors to the foamed composition. HFAs, particularly 1,1,1,2-Tetrafluoroethane (Freon-134a, HFC-134a), have no unpleasant odors associated with them and are preferred in the compositions described herein.

Furthermore, the compositions preferably contain no volatile alcohols or hydrocarbon propellant gases, which can produce flammable or explosive vapors during use. However, small amounts of such propellants may be used as adjunct propellants if required for particular formulations.

B. Keratolytic Agents

Suitable keratolytic agents include, but are not limited to, urea, salicylic acid, papain, sulfur, glycolic acid, pyruvic acid, resorcinol, N-acetylcysteine, retinoids such as retinoic acid and its derivatives (e.g., cis and trans, esters), alpha hydroxy acids, beta hydroxy acids, coal tar, and combinations thereof The concentration of the keratolytic agent is from about 1% to about 60% by weight of the final composition.

In one embodiment, the keratolytic agent is urea. Urea is present in an amount from about 5% to about 50%, preferably from about 10% to about 50%, more preferably from about 20% to about 40% by weight of the final composition. In another embodiment, ammonium lactate is added to a urea-containing formulation. Ammonium lactate is present in an amount from about 1% to about 30%, preferably from about 5% to about 20%, more preferably from about 10% to about 15% by weight of the final composition.

In another embodiment, the keratolytic agent is salicylic acid. Salicylic acid is present in an amount from about 1% to about 30%, preferably from about 4% to about 10%.

In another embodiment, the formulation comprises the enzyme papain and, optionally, urea. Papain is a proteincleaving enzyme derived from papaya and certain other plants. The concentration of papain is from about 0.5% to about 40%, preferably from about 1% to about 20%, more preferably from about 1% to about 10% by weight of the final composition. The concentration of urea is from about 1% to about 60%, preferably from about 2.5% to about 40%, more preferably from about 5% to about 15% by weight of the final composition.

In yet another embodiment, the composition comprises the enzyme papain in combination with urea and chlorophyllin copper complex sodium. The concentration of papain is from about 0.5% to about 40%, preferably from about 1% to about 20%, more preferably from about 1% to about 10% by weight of the final composition. The concentration of urea is from about 1% to about 60%, preferably from about 2.5%to about 40%, more preferably from about 5% to about 15% by weight of the final composition. The concentration of chlorophyll in copper complex sodium is from about 0.05% to about 5%, preferably from about 0.1% to about 3%, more preferably from about 0.3% to about 1% by weight of the final composition.

C. Other Active Agents

The compositions optionally contain one or more additional pharmaceutically active agents. Suitable classes of active agents include, but are not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, antiprotozoal agents, anti-oxidants, antihistamines, vitamins, and hormones.

i. Antibiotics

Representative antibiotics include, without limitation, benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate. The antibiotic can be an antifungal agent. Suitable antifungal agents include, but are not limited to, clotrimazole, econazole, ketoconazole, itraconazole, miconazole, oxiconazole, sulconazole, butenafine, naftifine, terbinafine, undecylinic acid, tolnaftate, and nystatin.

In one embodiment, the formulation contains one or more keratolytic agents in combination with an antibiotic agent. The concentration of the antibiotic is from about 0.01% to about 20%, preferably from about 1% to about 15%, more preferably from about 6% to about 12% by weight of the final composition.

ii. Non-Steroidal Anti-Inflammatory Agents

Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

iii. Steroidal Anti-Inflammatory Agents

Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

iv. Anesthetics

Representative anesthetics include, but are not limited to, lidocaine, bupivacaine, chlorprocaine, dibucaine, etidocaine, mepivacaine, tetracaine, dyclonine, hexylcaine, procaine, cocaine, ketamine, pramoxine and phenol.

v. Antimicrobial Agents

Suitable antimicrobial agents include, but are not limited to, antibacterial, antifungal, antiprotozoal and antiviral agents, such as beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, famesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, nystatin, tolnaftate, clotrimazole, anidulafungin, micafungin, voriconazole, lanoconazole, ciclopirox and mixtures thereof.

vi. Other Agents

Suitable other agents include, but are not limited to, deodorant agents, antiperspirants, sun screening agents, sunless tanning agents, vitamins, hair conditioning agents, anti-irritants, and combinations thereof.

Examples of skin soothing agents include, but are not limited to, aloe, avocado oil, green tea extract, hops extract, chamomile extract, colloidal oatmeal, calamine, cucumber extract, and combinations thereof.

Examples of vitamins include, but are not limited to, vitamins A, D, E, K, and combinations thereof.

Examples of sunscreens include, but are not limited to, p-Aminobenzoic acid, Avobenzone, Cinoxate, Dioxybenzone, Homosalate, Menthyl anthranilate, Octocrylene, Octyl methoxycinnamate, Octyl salicylate, Oxybenzone, Padimate O, Phenyl benzimidazole sulfonic acid, Sulisobenzone, Titanium dioxide, Trolamine salicylate, Zinc oxide, 4-methylbenzylidene camphor, Methylene Bis-Benzotriazolyl Tetramethylbutylphenol, Bis-Ethylhexyloxyphenol Methoxyphenyl Triazine, Terephthalylidene Dicamphor Sulfonic Acid, Drometrizole Trisiloxane, Disodium Phenyl Dibenzimidazole Tetrasulfonate, Diethylamine Hydroxybenzoyl Hexyl Benzoate, Octyl Triazone, Diethylhexyl Butamido Triazone, Polysilicone-15, and combinations thereof.

D. Excipients

The concentrate can be in the form of an emulsion. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of the propellant. Either or both of the oil phase and the aqueous phase may contain one or more excipients such as surfactants, emulsifiers, emulsion stabilizers, anti-oxidants, emollients, humectants, chelating agents, suspending agents, thickening agents, occlusive agents, preservatives, stabilizing agents, pH modifying agents, solubilizing agents, penetration enhancers, and other excipients.

Suitable emulsifiers include, but are not limited to, straight chain or branched fatty acids, polyoxyethylene sorbitan fatty acid esters, sorbitan fatty acid esters, propylene glycol stearate, glyceryl stearate; polyethylene glycol, fatty alcohols, polymeric ethylene oxide-propylene oxide block copolymers, and combinations thereof.

Suitable surfactants include, but are not limited to, anionic surfactants, non-ionic surfactants, cationic surfactants, and amphoteric surfactants. Examples of anionic surfactants include, but are not limited to, ammonium lauryl sulfate, sodium lauryl sulfate, ammonium laureth sulfate, sodium laureth sulfate, alkyl glyceryl ether sulfonate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium and ammonium salts of coconut alkyl triethylene glycol ether sulfate; tallow alkyl triethylene glycol ether sulfate, tallow alkyl hexaoxyethylene sulfate, disodium N-octadecylsulfosuccinnate, disodium lauryl sulfosuccinate, diammonium lauryl sulfosuccinnate, tetrasodium N-(1,2-dicarboxyethyl)-N-octadecylsulfosuccinnate, diamyl ester of sodium sulfosuccinic acid, dihexyl ester of sodium sulfosuccinic acid, dioctyl esters of sodium sulfosuccinic acid, docusate sodium, and combinations thereof.

Examples of nonionic surfactants include, but are not limited to, polyoxyethylene fatty acid esters, sorbitan esters, cetyl octanoate, cocamide DEA, cocamide MEA, cocamido propyl dimethyl amine oxide, coconut fatty acid diethanol amide, coconut fatty acid monoethanol amide, diglyceryl diisostearate, diglyceryl monoisostearate, diglyceryl monolaurate, diglyceryl monooleate, ethylene glycol distearate, ethylene glycol monostearate, ethoxylated castor oil, glyceryl monoisostearate, glyceryl monolaurate, glyceryl monomyristate, glyceryl monooleate, glyceryl monostearate, glyceryl tricaprylate/caprate, glyceryl triisostearate, glyceryl trioleate, glycol distearate, glycol monostearate, isooctyl stearate, lauramide DEA, lauric acid diethanol amide, lauric acid monoethanol amide, lauric/myristic acid diethanol amide, lauryl dimethyl amine oxide, lauryl/myristyl amide DEA, lauryl/myristyl dimethyl amine oxide, methyl gluceth, methyl glucose sesquistearate, oleamide DEA, PEG-distearate, polyoxyethylene butyl ether, polyoxyethylene cetyl ether, polyoxyethylene lauryl amine, polyoxyethylene lauryl ester, polyoxyethylene lauryl ether, polyoxyethylene nonylphenyl ether, polyoxyethylene octyl ether, polyoxyethylene octylphenyl ether, polyoxyethylene oleyl amine, polyoxyethylene oleyl cetyl ether, polyoxyethylene oleyl ester, polyoxyethylene oleyl ether, polyoxyethylene stearyl amine, polyoxyethylene stearyl ester, polyoxyethylene stearyl ether, polyoxyethylene tallow amine, polyoxyethylene tridecyl ether, propylene glycol monostearate, sorbitan monolaurate, sorbitan monooleate, sorbitan monopalmitate, sorbitan monostearate, sorbitan sesquioleate, sorbitan trioleate, stearamide DEA, stearic acid diethanol amide, stearic acid monoethanol amide, laureth-4, and combinations thereof.

Examples of amphoteric surfactants include, but are not limited to, sodium N-dodecyl-β-alanine, sodium N-lauryl-β-iminodipropionate, myristoamphoacetate, lauryl betaine, lauryl sulfobetaine, sodium 3-dodecyl-aminopropionate, sodium 3-dodecylaminopropane sulfonate, sodium lauroamphoacetate, cocodimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, oleamidopropyl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine, and combinations thereof.

Examples of cationic surfactants include, but are not limited to, behenyl trimethyl ammonium chloride, bis(acyloxyethyl)hydroxyethyl methyl ammonium methosulfate, cetrimonium bromide, cetrimonium chloride, cetyl trimethyl ammonium chloride, cocamido propyl amine oxide, distearyl dimethyl ammonium chloride, ditallowdimonium chloride, guar hydroxypropyltrimonium chloride, lauralkonium chloride, lauryl dimethylamine oxide, lauryl dimethylbenzyl ammonium chloride, lauryl polyoxyethylene dimethylamine oxide, lauryl trimethyl ammonium chloride, lautrimonium chloride, methyl-1-oleyl amide ethyl-2-oleyl imidazolinium methyl sulfate, picolin benzyl ammonium chloride, polyquaternium, stearalkonium chloride, stearyl dimethylbenzyl ammonium chloride, stearyl trimethyl ammonium chloride trimethylglycine, and combinations thereof.

Suitable suspending agents include, but are not limited to, alginic acid, bentonite, carbomer, carboxymethylcellulose and salts thereof, colloidal oatmeal, hydroxyethylcellulose, hydroxypropylcellulose, microcrystalline cellulose, colloidal silicon dioxide, dextrin, gelatin, guar gum, xanthan gum, kaolin, magnesium aluminum silicate, maltitol, triglycerides, methylcellulose, polyoxyethylene fatty acid esters, polyvinylpyrrolidone, propylene glycol alginate, sodium alginate, sorbitan fatty acid esters, tragacanth, and combinations thereof.

Suitable antioxidants include, but are not limited to, butylated hydroxytoluene, alpha tocopherol, ascorbic acid, fumaric acid, malic acid, butylated hydroxyanisole, propyl gallate, sodium ascorbate, sodium metabisulfite, ascorbyl palmitate, ascorbyl acetate, ascorbyl phosphate, Vitamin A, folic acid, flavons or flavonoids, histidine, glycine, tyrosine, tryptophan, carotenoids, carotenes, alpha-Carotene, beta-Carotene, uric acid, pharmaceutically acceptable salts thereof, derivatives thereof, and combinations thereof.

Suitable chelating agents include, but are not limited to, EDTA, disodium edetate, trans-1,2-diaminocyclohexane-N,N,N',N'-tetraaceticacid monohydrate, N,N-bis(2-hydroxyethyl)glycine, 1,3-diamino-2-hydroxypropane-N,N,N',N'-tetraacetic acid, 1,3-diaminopropane-N,N,N',N'-tetraacetic acid, ethylenediamine-N,N'-diacetic acid, ethylenediamine-N,N'-dipropionic acid, ethylenediamine-N,N'-bis(methylenephosphonic acid), N-(2-hydroxyethyl)ethylenediamine-N,N',N'-triacetic acid, ethylenediamine-N,N,N',N'-tetrakis (methylenephosponic acid), O,O'-bis(2-aminoethyl) ethyleneglycol-N,N,N',N'-tetraacetic acid, N,N-bis(2-hydroxybenzyl)ethylenediamine-N,N-diacetic acid, 1,6-hexamethylenediamine-N,N,N',N'-tetraacetic acid, N-(2-hydroxyethyl)iminodiacetic acid, iminodiacetic acid, 1,2-diaminopropane-N,N,N',N'-tetraacetic acid, nitrilotriacetic acid, nitrilotripropionic acid, nitrilotris(methylenephosphoric acid), 7,19,30-trioxa-1,4,10,13,16,22,27,33-octaazabicyclo[11,11,11] pentatriacontane hexahydrobromide, triethylenetetramine-N,N,N',N'',N''',N'''-hexaacetic acid, and combinations thereof.

Suitable emollients include, but are not limited to, myristyl lactate, isopropyl palmitate, light liquid paraffin, cetearyl alcohol, lanolin, lanolin derivatives, mineral oil, petrolatum, cetyl esters wax, cholesterol, glycerol, glycerol monostearate, isopropyl myristate, lecithin, and combinations thereof.

Suitable humectants include, but are not limited to, glycerin, butylene glycol, propylene glycol, sorbitol, triacetin, and combinations thereof.

The compositions described herein may further contain sufficient amounts of at least one pH modifier to ensure that the composition has a final pH of about 3 to about 11. Suitable pH modifying agents include, but are not limited to, sodium hydroxide, citric acid, hydrochloric acid, acetic acid, phosphoric acid, succinic acid, sodium hydroxide, potassium hydroxide, ammonium hydroxide, magnesium oxide, calcium carbonate, magnesium carbonate, magnesium aluminum silicates, malic acid, potassium citrate, sodium citrate, sodium phosphate, lactic acid, gluconic acid, tartaric acid, 1,2,3,4-butane tetracarboxylic acid, fumaric acid, diethanolamine, monoethanolamine, sodium carbonate, sodium bicarbonate, triethanolamine, and combinations thereof.

Preservatives can be used to prevent the growth of bacteria, fungi and other microorganisms. Suitable preservatives include, but are not limited to, benzoic acid, butylparaben, ethyl paraben, methyl paraben; propylparaben, sodium benzoate, sodium propionate, benzalkonium chloride, benzalkonium chloride, benzyl alcohol, cetypyridinium chloride, chlorobutanol, phenol, phenylethyl alcohol, thimerosal, and combinations thereof.

II. Method of Making the Formulation

A. Method of Preparing An Emulsion Concentrate

The oil phase is prepared by mixing together the surfactant(s) and emulsifier(s), and heating if necessary. The aqueous phase is prepared separately by dissolving the propylene glycol and preservatives in water with heating: The oil phase is added to the aqueous phase with continuous high shear mixing to produce a milky emulsion. The emulsion is cooled and if necessary, the pH is adjusted by the addition of a pH modifying agent.

If desired, the active agent(s) can be separately suspended or dissolved in water and/or propylene glycol and treated to eliminate any large aggregates. In a small scale operation, the mixture can be milled. The final active agent particle size is small enough to allow aerosolization, for example, less than about 20 microns in diameter, preferably less than about 10 microns, more preferably, less than about 5 microns. The liquid containing the active agent is added to the emulsion with mixing. Alternatively, the active agent can be added directly to the water phase prior to emulsification. The formulation is brought to the final weight by the addition of water.

The concentration of the surfactant(s) in the concentrate is from about 0.5 to about 15% by weight of the final composition. The concentration of the emulsifier(s) is from about 0.5% to about 5% by weight of the final composition. The concentration of the pH modifying agent(s) is from about 0.1% to about 5% by weight of the final composition. The concentration of the preservative(s) is from about 0.01% to about 1% by weight of the final composition.

B. Method of Preparing the Formulation

The emulsion concentrate is placed in pressure cans, preferably coated aluminum cans to prevent corrosion, such as epoxy-coated cans. The lid and dispensing apparatus are crimped in place. The can is charged with propellant to the stated level, for example, by adding 10 grams of propellant per 90 grams of emulsion. At the time of application, the mixture of the emulsion with the propellant may be insured by shaking, optionally with the aid of a mixing bead. The dispenser may be metered or unmetered (continuous). The can may be arranged for either "upside down" spraying with the valve at the bottom, or the can have a dip tube so that the foam can be sprayed while the can is upright with the valve at the top. In one embodiment, the concentration of the HFC propellant(s) is from about 5% to about 40% by weight of the final composition, more preferably about 5% to about 20% by weight of the final composition. In another embodiment, the emulsion concentrate is mixed with an HFC propellant so that the final formulation in an aerosol can comprises about 90% to about 95% of concentrate and about 5% to about 10% of propellant.

In certain embodiments, the invention relates to a method of making a topical foam aerosol formulation, the method comprising:

(a) making an oil in water emulsion with a predominantly, more than 50%, aqueous phase;

(b) dissolving or dispersing one or more keratolytic agents in the aqueous phase or oil phase prior to emulsification; and (c) adding a propellant consisting essentially of a hydrofluoroalkane or a mixture of hydrofluoroalkanes, without additional co-solvents or co-propellants, to the emulsion, wherein the emulsion produces an immediate foaming action on expulsion from a pressurized container.

C. Foam Viscosity

In one embodiment, the foam has a sufficiently high viscosity to prevent the formulation from "running off" the site of application. The formulation also preferably has a sufficiently low viscosity that the formulation efficiently releases the actives to the treatment site. These contrasting attributes can be realized in a shear-thinning foam. "Shear-thinning" describes the rheological condition where the viscosity of a material subjected to constant shear stress decreases. The amount of decrease in viscosity is a function of the degree of shear stress applied. Upon removal of the shear stress, the viscosity again increases to the original value over time. Two values are of particular importance in developing shear-thinning formulations for hyperkeratotic conditions. These are the zero shear viscosity and the yield stress. The zero shear viscosity dictates the resistance of the formulation to flow after application and ability of the formulation to release actives. The yield stress defines the stress level at which the material transitions from a "solid-like" poorly flowing high viscosity foam to a "liquid-like" well flowing low viscosity foam. The lower the yield stress, the easier it is to uniformly spread and rub-in the formulation over the treatment site.

Foam rheology is a function of the composition of the foam base and the expansion factor of the foam. Expansion factor is the volume a given mass of foam occupies and is the reciprocal of the foam density. Foam expansion factor is determined by the foam base composition and the composition and concentration of propellant. For a given foam base and propellant composition, changes in the expansion factor of the foam can be achieved by varying the concentration of propellant.

For topical foam products, the zero shear viscosity of the dispensed foam is between 15,000 and 700,000 cP. In certain embodiments, the zero shear viscosities are preferably greater than about 30,000 cP, more preferably greater than about 45,000 cP, and most preferably greater than about 60,000 cP; and also less than about 700,000 cP, more preferably less than about 500,000 cP and still more preferably less than about 300,000 cP. The preferred yield stress values are preferably greater than about 250 dynes/cm$^2$, more preferably greater than about 750 dynes/cm$^2$, and most preferably greater than about 1000 dynes/cm$^2$, and also preferably lower than about 60,000 dynes/cm$^2$, more preferably lower than about 30,000 dynes/cm$^2$, and still more preferably lower than about 10,000 dynes/cm$^2$. The preferred foam expansion factor is from 1.5 to 15 cm$^3$/g, more preferably from 1.8 to 10 cm$^3$/g, most preferably from 2.0 to 7.0 cm$^3$/g. In certain embodiments, the foam density is from about 0.1 g/mL to about 0.6 g/mL.

III. Mode of Administration a. Method of Administration to a Patient

The formulation is administered to the skin or wound of a human or animal. A selected amount of product is dispensed from the spray can, preferably onto the site to be treated. The foam can be administered into the palm of the hand. Alternatively, the foam can be applied to a wound dressing. The amount to be delivered can be determined by the prescribing physician or as directed in the instructions for non-prescription products. Alternatively, a fixed dose using the metering dispenser can be administered. The foam is rubbed into the skin at the site to be treated. Because the foam is stable at body temperature, this step does not need to be hurried. Moreover, the exact site of application can be more easily controlled. If contact with the hand is to be avoided, a glove may be worn; or, the foam can be first be applied to a wound dressing or may be left in place, wherein it will eventually collapse and deliver the active ingredient to the surface of the skin.

EXAMPLES

Example 1

Reduced Odor Topical Formulation Containing Sulfur and Sodium Sulfacetamide

A topical formulation containing sulfur and sodium sulfacetamide was prepared wherein the formulation exhibited diminished color. The composition of the formulation and the physical and mechanical properties of the formulation are shown in Table 1.

The formulation was prepared by mixing the water and propylene glycol together and adding the methylparaben, propylparaben and sodium sulfacetamide to form a uniform solution. The solution was heated to 70° C. and the sulfur was dispersed in the solution with moderate stirring. Separately, cetyl alcohol, emulsifying wax, and BRIJ 76 were melted together and heated to 70° C. The water and oil phases were combined and mixed for 10 minutes at high shear to form the emulsion. The emulsion was allowed to cool to 45° C. with moderate stirring at which time trolamine was added to the formulation and the formulation was adjusted to 100% with water.

The final formulation consisted of 91% by weight emulsion concentrate and 9% by weight HFC 134a propellant.

Example 2

Reduced Odor Topical Formulation Containing Urea

A topical formulation containing urea was prepared, wherein the formulation exhibited diminished odor. The composition of the formulation and the physical and mechanical properties of the formulation are shown in Table 1.

The formulation was prepared by mixing the water and propylene glycol together and adding the methylparaben, propylparaben and urea to form a uniform solution. The solution was heated to 70° C. with moderate stirring. Separately the cetyl alcohol, emulsifying wax and BRIJ 76 were melted together and heated to 70° C. The water and oil phases were combined and mixed for 10 minutes at high shear to form the emulsion. The emulsion was allowed to cool to 45° C. with moderate stirring at which time the trolamine was added and the formulation was adjusted to 100% with water.

The final formulation consisted of 91% by weight emulsion concentrate and 9% by weight HFC 134a propellant.

TABLE 1

Formulation Composition and Physical and Mechanical Properties of Examples 1 and 2

| Ingredient | Example 1 (w/w %) | Example 2 (w/w %) |
|---|---|---|
| Propylene Glycol USP | 10 | 10.1 |
| Cetyl Alcohol, NF | 0.7 | 0.75 |
| Trolamine, NF | 0.1 | 0.1 |
| Emulsifying Wax, NF | 1.5 | 1.5 |
| BRIJ 76 | 0.5 | 0.5 |
| Water | 72.06 | 76.905 |
| Methylparaben, USP/NF | 0.11 | 0.11 |
| Propylparaben, USP/NF | 0.03 | 0.035 |
| Na Sulfacetamide, USP | 10 | 0 |
| Sulfur, USP | 5 | 0 |
| Urea, USP | 0 | 10 |
| Total | 100 | 100 |

TABLE 1-continued

Formulation Composition and Physical and Mechanical Properties of Examples 1 and 2

| Mechanical Property | Example 1 | Example 2 |
|---|---|---|
| Foam Yield Stress | 2074 dynes/cm$^2$ | 2143 dynes/cm$^2$ |
| Foam Flow Index | 0.525 | 0.582 |
| Foam Zero Shear Viscosity | 105600 cP | 118200 cP |
| Conc Yield Stress | 7081 dynes/cm$^2$ | 3355 dynes/cm$^2$ |
| Conc Consistency Index | 17286 cP | 13511 cP |
| Conc Flow Index | 0.2818 | 0.397 |
| Conc Zero Shear Viscosity | 169600 cP | 106400 cP |
| Conc Infinite Shear Viscosity | 1884 cP | 3017 cP |

Example 3

Organoleptic Analysis of Formulation Odor and Color

The odor and color of the formulations outlined in Table 1 were measured. Samples of the sulfur and urea aerosol foams were dispensed into weighing boats in a manner similar to that used to dispense the product for use. The samples of sulfur and urea emulsion concentrates were observed for color and odor in bulk packaging under conditions similar to that in which currently marketed products are used. Panelists were asked to rate on a scale of 0 to 5 each sample for the attributes of color and odor. In the scale, 0 corresponded to no detectable odor or color and 5 corresponded to strong odor or color. The results are shown in Table 2.

TABLE 2

Organoleptic Analysis of Formulation Odor and Color

| | Sulfacetamide/Sulfur | | | | Urea | |
|---|---|---|---|---|---|---|
| | Foam | | Concentrate | | Foam | Concentrate |
| | Odor Score | Color Score | Odor Score | Color Score | Odor Score | Odor Score |
| Average | 0.7 | 1.5 | 2.0 | 3.9 | 0.1 | 4.3 |
| Std Dev | 0.8 | 0.8 | 1.2 | 1.1 | 0.3 | 1.3 |
| p value | 0.0005 | 0.0001 | n/a | n/a | </=0.0001 | n/a |
| n | 10 | 10 | 10 | 10 | 10 | 10 |

Example 4

Reduced Odor Topical Formulation Containing Papain and Urea

A topical formulation containing papain and urea was prepared, wherein the formulation exhibited diminished color. The composition of the formulation is shown in Table 3.

The formulation was prepared by mixing the water and propylene glycol together and adding methylparaben, propylparaben, lactose, urea and sodium phosphate monobasic to form a uniform solution. The solution was then heated to 70° C. with moderate stirring. Separately the cetyl alcohol, emulsifying wax and BRIJ 76 were melted together and heated to 70° C. The water and oil phases were combined and mixed for 10 minutes at high shear to form the emulsion. The emulsion was then allowed to cool to 45° C. with moderate stirring at which time the papain was added and the formulation was adjusted to 100% with water.

The final formulation consisted of 91% by weight emulsion concentrate and 9% by weight HFC 134a propellant.

TABLE 3

Papain-Urea Formulation Composition

| Ingredient | Example 4 (w/w %) |
|---|---|
| Propylene Glycol USP | 5 |
| Cetyl Alcohol, NF | 0.7 |
| Sodium Phosphate monobasic | 0.1 |
| Glycerol, USP | 5 |
| Lactose, USP | 1 |
| Sodium Bisulfite | 1 |
| Emulsifying Wax, NF | 1.5 |
| BRIJ 76 | 0.5 |
| Water | 72.26 |
| Methylparaben, USP/NF | 0.11 |
| Propylparaben, USP/NF | 0.03 |
| Papain, USP | 2.8 |
| Urea, USP | 10 |

Example 5

Salicylic Acid Foam Formulation

A concentrate was prepared containing the following ingredients:

| Ingredient | % W/W |
|---|---|
| Crodafos CS 20A | 1 |
| Cetostearyl Alcohol | 0.5 |
| Crodafos CES | 1 |
| Tocopheryl Acetate USP | 0.5 |
| White Petrolatum | 0.5 |
| DI Water | 66.92 |
| Glycerin USP | 5 |
| Disodium EDTA | 0.05 |
| Aloe (Aloe Vera Gel) | 0.1 |
| 5N Sodium Hydroxide solution | 0.4 |
| Salicylic Acid USP | 6 |
| Ammonium Lactate | 5 |
| 5N Sodium Hydroxide solution | 10.807 |
| Propylene Glycol USP | 3 |
| Methyl Paraben | 0.3 |
| Propyl Paraben | 0.03 |
| Total | 100 |

The concentrate and foam were prepared as described in Examples 1 and 2.

Unless defined otherwise, all technical and scientific terms used herein have the same meanings as commonly understood by one of skill in the art to which the disclosed invention belongs. Publications cited herein and the material for which they are cited are specifically incorporated by reference. Those skilled in the art will recognize, or be able to ascertain using no more than routine experimentation, many equivalents to the specific embodiments of the invention described herein. Such equivalents are intended to be encompassed by the following claims.

We claim:

1. A method of treating a skin condition, comprising the steps of:
    (i) providing, in a pressurized aerosol container, an aerosol formulation comprising:
        (a) an oil-in-water emulsion, wherein the oil-in-water emulsion comprises an oil phase and an aqueous phase; and
        (b) a propellant comprising a hydrofluoroalkane contacting the emulsion; and (c) sulfur dissolved or dispersed in the oil-in-water emulsion, (ii) expelling from the pressurized aerosol container the aerosol formulation, wherein the step of expelling the aerosol formulation produces an immediate foaming action, thereby forming a foam, and (iii) administering topically to an area of skin of a human in need thereof an effective amount of the foam, wherein the aerosol formulation does not comprise urea, ethanol, or a hydrocarbon propellant;

the oil phase comprises emulsifying wax, polyoxyethylene stearyl ether, and cetyl alcohol;

the aqueous phase comprises water, propylene glycol, methylparaben, propylparaben, sodium sulfacetamide, and a pH modifying agent;

the propellant is about 5% to about 30% by weight of the aerosol formulation prior to expulsion from the pressurized container;

the foam has no odor and no color;

the foam is stable for at least 5 minutes at body temperature;

the foam has a yield stress between 250 and 60,000 dynes/cm$^2$;

the foam has an expansion factor between 1.5 and 15 cm$^3$/g;

the foam has a zero shear viscosity between 15,000 and 700,000 cP;

the foam has a foam density from about 0.1 g/mL to about 0.6 g/mL; and the skin condition is selected from the group consisting of a fungal infection, corns, warts, acne, rosacea, seborrheic dermatitis, eczema, xerosis, scabies, pediculosis, and psoriasis.

2. The method of claim 1, wherein the concentration of sulfur in the aerosol formulation is about 1% to 60%.

3. The method of claim 1, wherein the foam is stable for at least 20 minutes at body temperature.

4. The method of claim 1, wherein the amounts of sulfur and sodium sulfacetamide are each about 0.01% to about 20% (w/w) of the aerosol formulation.

5. The method of claim 1, wherein the amounts of sulfur and sodium sulfacetamide are each about 1% to about 15% (w/w) of the aerosol formulation.

6. The method of claim 1, wherein the amounts of sulfur and sodium sulfacetamide are each about 6% to about 12% (w/w) of the aerosol formulation.

7. The method of claim 1, wherein the hydrofluoroalkane is selected from the group consisting of 1,1,1,2-tetrafluoroethane (134a); 1,1,1,2,3,3,3-heptafluoropropane (227); and combinations thereof.

8. The method of claim 1, wherein the pH modifying agent is about 0.1% to about 5% by weight of the oil-in-water emulsion.

* * * * *